(12) United States Patent
Joksch

(10) Patent No.: US 11,603,517 B2
(45) Date of Patent: Mar. 14, 2023

(54) METHOD FOR MONITORING A BIOTECHNOLOGICAL PROCESS

(71) Applicant: Siemens Aktiengesellschaft, Munich (DE)

(72) Inventor: Martin Joksch, St. Andrä-Wördern (AT)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 797 days.

(21) Appl. No.: 16/500,692

(22) PCT Filed: Apr. 3, 2018

(86) PCT No.: PCT/EP2018/058396
§ 371 (c)(1),
(2) Date: Oct. 3, 2019

(87) PCT Pub. No.: WO2018/185052
PCT Pub. Date: Oct. 11, 2018

(65) Prior Publication Data
US 2020/0190460 A1    Jun. 18, 2020

(30) Foreign Application Priority Data

Apr. 4, 2017 (EP) .................................. 17164767

(51) Int. Cl.
*C12M 1/34* (2006.01)
*G01N 15/06* (2006.01)
*G01N 21/3504* (2014.01)

(52) U.S. Cl.
CPC ............ *C12M 41/36* (2013.01); *C12M 41/32* (2013.01); *C12M 41/34* (2013.01); *C12M 41/38* (2013.01);
(Continued)

(58) Field of Classification Search
CPC ...... C12M 41/00; C12M 41/32; C12M 41/38; C12M 41/34; C12M 41/36; G01N 21/3504; G01N 15/06
See application file for complete search history.

(56) References Cited

U.S. PATENT DOCUMENTS

| 4,810,650 A | * | 3/1989 | Kell | ................. | G01N 33/48735 |
| | | | | | 324/683 |
| 4,965,206 A | * | 10/1990 | Kell | ................. | G01N 33/48735 |
| | | | | | 435/39 |

(Continued)

FOREIGN PATENT DOCUMENTS

| CN | 101939408 | 1/2011 |
| CN | 103814138 | 5/2014 |

(Continued)

OTHER PUBLICATIONS

PCT International Search Report dated May 8, 2018 based on PCT/EP2018/058396 filed Apr. 3, 2018.

*Primary Examiner* — Sang H Nguyen
(74) *Attorney, Agent, or Firm* — Cozen O'Connor

(57) ABSTRACT

A method for monitoring a biotechnological process, wherein starting materials are converted into products via a biomass and important process parameters for monitoring are identified during the process, where during the process, a current concentration of the biomass utilized in the process is recurrently estimated, current measurement values of measurable process parameters are then recurrently determined on a recurring basis and current values for additional process parameters are identified therefrom, where the current measurement values of the measurable process parameters and the current determined values of the additional process parameters are based on the respective temporally correlating concentration of biomass and where, from a combination of the current concentration of biomass and the (Continued)

current measurement values of the measurable process parameters and the identified current values of the additional process parameters, current, cell-specific metabolic indicators are then derived which are then used in conjunction with a deterministic process model.

15 Claims, 2 Drawing Sheets

(52) U.S. Cl.
CPC ......... *G01N 15/06* (2013.01); *G01N 21/3504* (2013.01)

(56) References Cited

U.S. PATENT DOCUMENTS

| | | | |
|---|---|---|---|
| 2004/0227947 A1* | 11/2004 | Navarro Herrero | C12Q 1/06 356/432 |
| 2011/0035157 A1* | 2/2011 | Munoz Berbel | C12M 41/36 702/19 |
| 2013/0030715 A1 | 1/2013 | Tixier et al. | |
| 2014/0343872 A1 | 11/2014 | Ilmola et al. | |
| 2015/0099274 A1* | 4/2015 | Axelrod | C12M 41/46 435/39 |
| 2016/0130629 A1* | 5/2016 | Sirois | G01N 21/6486 435/29 |

FOREIGN PATENT DOCUMENTS

| | | |
|---|---|---|
| CN | 103959059 | 7/2014 |
| DE | 102004031249 | 1/2006 |
| EP | 0616171 | 9/1994 |
| EP | 0821232 | 1/1998 |
| EP | 1455983 | 9/2004 |
| EP | 2050812 | 4/2009 |
| WO | WO2004/018692 | 3/2004 |

* cited by examiner

METHOD FOR MONITORING A BIOTECHNOLOGICAL PROCESS

CROSS-REFERENCE TO RELATED APPLICATIONS

This is a U.S. national stage of application No. PCT/EP2018/058396 filed Apr. 3, 2018. Priority is claimed on EP Application No. 17164767 filed Apr. 4, 2017, the content of which is incorporated herein by reference in its entirety.

BACKGROUND OF THE INVENTION

1. Field of the Invention

The present invention generally relates to the field of biotechnology and bioengineering and more particularly, to a method for monitoring a biotechnological process, where during a start of a process materials are converted into products via a biomass, such as living cells and/or microorganisms, and important process parameters for monitoring are identified.

2. Description of the Related Art

Nowadays biotechnological processes are used in various areas, such as the food and beverage industry, the biopharmaceutical industry, or in the production of biofuels. Biotechnological processes such as in particular, fermentation processes form, for example, a key technology in the production of beer, whisky or wine, in the production of biofuel or in the manufacture of vaccines or antibiotics. In biotechnological processes such as fermentation, organic starting materials of a substrate, such as sugar, or glucose are usually converted with the aid of biomass via enzymatic conversion into products, such as alcohol, acids, or gases. A biotechnological process and/or fermentation is deliberately triggered by the addition of the biomass to a substrate. In biotechnological processes, for example, living cells and/or microorganisms, such as bacteria, fungi or other biological cell, cultures are used as biomass.

The biotechnological processes usually occurs in bioreactors in which the ambient and reaction conditions for the respective biotechnological process can be controlled and optimized. For fermentation processes, the bioreactors are also referred to as fermenters. In order to obtain the substance to be produced from the biomass used under the most optimal conditions or in the desired concentration, corresponding environmental and/or process parameters for the respective biotechnological process, such as pH value, temperature, oxygen supply, nitrogen supply, glucose content or stirring settings, are regulated and controlled in the bioreactor. Biotechnological processes are biologically complex and very sensitive, however. Therefore, ongoing detailed monitoring of a biotechnological process is necessary to ensure the corresponding environmental conditions in the bioreactor for a consistent and optimum course of the process and so that the biomass used can grow in the nutrient solution and produce the desired substance.

For an optimization of biotechnological processes, an exact knowledge of the biochemical metabolic processes is furthermore necessary to achieve the highest yields with the lowest consumption of resources. However, an ongoing detailed monitoring and control of biotechnological processes and in particular, of biochemical metabolic processes, is not easy to realize. Many of the process parameters and cell-specific indicators required for this purpose, such as a concentration of metabolites (metabolites are starting materials or products and/or intermediate products from enzymatic reactions which occur naturally in cells and/or microorganisms, or a concentration of the product and thus also conversion rates) cannot be measured directly.

Nowadays, biotechnological processes are frequently operated and controlled from a plant perspective. That is, in today's plants and/or bioreactors, for example, via a "closed loop" control system, environmental conditions (e.g. temperature, pH, or oxygen content) are set to a particular value and usually kept constant. The nutritional addition required for the particular process is frequently controlled by a defined "feed strategy". Furthermore, for example, process parameters, such as base consumption, oxygen consumption and carbon dioxide emission are, measured for regulation, and to obtain derived quantities for biomass behavior or cell behavior.

In such process management and monitoring, however, the biochemical processes are not individually monitored and regulated, but usually only one sum is detected. The exact settings for the environmental conditions, i.e., the exact settings for, for example, temperature, pH, oxygen content, or strategy for nutritional addition, are usually set in process development. That is, the settings are determined and optimized for specific process management, for example, via mathematical modeling of the process, where the process is then controlled during production only based on the predetermined settings. However, the process cannot be changed anymore.

However, if during the course of the process changes which cannot be influenced occur in the production conditions, such as a change in the composition of production solution, nutrient or medium or in the behavior of the organisms employed, then this can lead to losses in the yield and/or the process may eventually become ever further removed from the optimum set in process development. Different causes may exist for the losses and/or deviations, such as errors in the process (for example, impurities, or incorrect fumigation), biological variability (for example, differences in the preculture of the biomass used; differences in the cell strain, etc.) or variability in process management (for example, differences in raw materials, variations in substrate composition, differences in technical equipment). These different causes are often difficult to determine and hard to correct as data and characteristic values for underlying biochemical and/or biological processes are missing. Furthermore, for example, measurement errors of sensors (for example, drift during production) or errors in control mechanisms are difficult to detect in some cases.

At present, however, little or no information about cell-specific metabolic indicators that could be used for corrective regulation and control of a biotechnological process is directly available in the course of a biotechnological process.

SUMMARY OF THE INVENTION

In view of the foregoing, it is therefore an object of the invention to provide a method for monitoring a biotechnological process, where cell-specific metabolic indicators that can be used for process development, as well as for process management, can be determined in a simple and reliable manner during the process.

This and other objects and advantages are achieved in accordance with the invention by a method from which a current concentration of the biomass used in the process is periodically recurrently estimated during the course of a biotechnological process. Current measurement values of measurable process parameters are then recurrently determined and current values for additional process parameters are identified therefrom. Subsequently, the current measurement values of the measurable process parameters and the current determined values of the additional process parameters are based on the respective temporally correlating concentration of biomass. That is, in a periodically recurring measuring cycle, first a current biomass concentration and then accordingly current measurement values of measurable process parameters and current values determined therefrom are determined by additional process parameters and then combined with one another. From a combination of the current concentration of biomass and the current measurement values of the measurable process parameters and the identified current values of the additional process parameters, current, cell-specific metabolic indicators are then derived. The current, cell-specific metabolic indicators are then used in conjunction with a "deterministic process model".

The main aspect of the disclosed method in accordance with the invention is that the current, cell-specific metabolic indicators available provide direct information on cell biological variables for virtually any time in the biotechnological process. The cell-specific metabolic indicators may include, for example, cell-specific uptake rates of oxygen and nutrients (for example, glucose), cell-specific conversion or production rates, specific cell growth, or cell-specific carbon dioxide emissions. Thus, during the process, reliable current values for cell parameters are obtained as current, cell-specific metabolic indicators, enabling a biological or biochemical view of the respective biotechnological process, in particular, associated cell metabolism. The current, cell-specific metabolic indicators can then be employed in conjunction with the deterministic process model.

With the aid of the deterministic process model, metabolic and catabolic processes can be described during a biotechnological process. Conventional biochemical processes are described inside and outside the respectively employed bioactive cells (biomass) of the respective biotechnological process via mathematical equations, such as differential equations, in order, for example, to be able to predict values of important process parameters (for example, glucose concentration, ethanol concentration, or biomass) at any time. The initial values for the deterministic process model can be, for example, an initial value of the biomass as well as an initial value of a nutrient (for example, glucose) weighed for the respective biotechnological process.

Furthermore, the method in accordance with the invention offers the advantage that decisions and adjustments of the process can be implemented very simply based on current, process-specific biological or biochemical information. With the method in accordance with the invention, for example, the concentration of the biomass, the concentrations of the metabolites and the conversion or production rates are known at any time of a biotechnological process and can optionally also be adjusted directly. Furthermore, based on the current, cell-specific metabolic indicators, in particular in conjunction with the so-called deterministic process model, it is possible to draw conclusions about any measurement errors or sensor defects that have occurred.

It is favorable if the current values of the additional process parameters are calculated from the measured actual values of the measurable process parameters via a "balancing process model". With the balancing process model, a material balance is produced via the respective biotechnological process from measurement values of measurable process parameters. For this purpose, chemical equations are used via which individual metabolic pathways for metabolism and anabolism (i.e., cell growth) of the respective process are described. The balancing process model has the advantage that current values for additional process parameters can be determined without specifying starting conditions. That is, even with unknown or varying starting conditions, values for additional process parameters can be determined very easily from the measurement values of the measurable process parameters.

Process parameters for which current measurable values can be determined almost in real time during the biotechnological process are ideally used as measurable process parameters. Such measurable process parameters are, for example, oxygen consumption and/or carbon dioxide emissions, the current measurement values of which can be determined very easily via "off-gas analysis". The current measurement values of oxygen consumption and carbon dioxide emission then represent, for example, input parameters for the balancing process model to determine current values of additional process parameters. Other measurable process parameters that can likewise be used in the method in accordance with the invention are, for example, a base consumption or an acid consumption per biotechnological process.

As additional process parameters, consumption and production quantities that can be derived in a simple manner are used as additional process parameters. Such derivable consumption and production variables are, for example, nutrient consumption, in particular, glucose consumption, substance production and/or biomass growth as well as current substance conversion rates or production rates. The current values of these additional production parameters are determined with the help of the balancing process model.

Furthermore, it is advantageous if a suitable sensor system is used for estimating the respective current concentration of the biomass. As a suitable sensor for estimating the concentration of biomass during the course of the process, for example, a system for measuring the cell density of living cells and/or microorganisms (for example, Incyte from the company Hamilton) can be used. Such a system is based, for example, on the fact that living cells behave like small capacities and their polarization and depolarization can be measured in a variable electric field. The cell density of the biomass or a biovolume can be determined from the measured signal in the course of the process and thus an actual concentration of the biomass estimated.

Alternatively, or additionally, a "statistical model" can also be used to estimate the respective current concentration of the biomass. In the mathematical modeling of a statistical model, historical or static data of the respective bioprocess (for example, values of measurable process parameters, such as oxygen consumption, base consumption, carbon dioxide emission and respiratory quotient) are usually used. In the case of, for example, an assumption of a constant biotechnological process, a current concentration of the biomass in the bioreactor can be estimated or predicted for a measurement time using the static model. A "Partial Least Squares" or PLS model, for example, can be used as a statistical model.

An expedient embodiment of the method in accordance with the invention provides that the current, cell-specific metabolic indicators are compared with time-correlated, calculated comparative values for these cell-specific, metabolic indicators. The deterministic process model can be used for a calculation of the comparative values. If there is a difference between the current, cell-specific metabolic key figures and the time-correlated calculated reference values, appropriate correction and/or verification measures can be initiated. It is particularly advantageous that the difference between the current, cell-specific metabolic indicators and the time-correlated comparative values from the deterministic process model can be used to conclude measuring errors in sensors used.

In this way, even small errors or fluctuations can be rapidly detected as here the currently determined cell-specific, metabolic indicators are compared with comparative values. If the differences or deviations are greater than expected statistical fluctuations, then this can, for example, already be considered as an error, and an intervention in the process undertaken correspondingly quickly.

If a difference between the current, cell-specific metabolic indicators and the time-correlated comparative values calculated using the deterministic process model, for example greater than expected statistical fluctuations, is established, then it can be concluded from this that the biomass, for example, behaves differently than assumed. If necessary, a readjustment can then be made in the course of the biotechnological process.

Furthermore, it is possible to conclude measurement errors of individual sensors (for example, oxygen probe, or $CO_2$ probe) based on the differences or deviations between the current, cell-specific metabolic indicators and the time-correlated comparative values calculated using the deterministic process model. For this purpose, for example, it is possible to calculate back to input values for the respective time based on the value combination and to check whether such an input value combination is chemically and/or physically possible (such as a negative value for the biomass).

Alternatively or additionally, it may be advantageous if the current cell-specific metabolic indicators are used as initial values or input values for a deterministic process model, these values resulting from the statistical and/or balancing process models. Here, the respective current, cell-specific metabolic indicators are accepted into the deterministic process model to predict, for example, a further course of the process, a time for a process end or an expected process quantity. Thus, especially in a process development, effects of altered environmental conditions (for example, temperature, pH, or oxygen supply) can be estimated quickly and easily or a deterministic process model can be very easily parameterized for a new process (for example, with a new biomass).

In a preferred embodiment of the method in accordance with the invention, a time frequency for estimating the respective current concentration of the biomass and the determination of the current measurement values of the measurable process parameters and the current values of the additional process parameters, i.e., the time repetition frequency of a measuring cycle, is established as a function of the biomass. That is, the repetition frequency can be adjusted to the respective biotechnological process or the course of its process to obtain the optimum number of current values for the respective process.

Ideally, the current, cell-specific metabolic indicators are output on a display unit. Thus, during the process, an operator always has current values of the cell-specific metabolic indicators available, for example, to monitor the biotechnological process, to directly regulate individual process parameters or to be able to recognize deviations immediately.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention is explained by way of example hereinafter with reference to the accompanying Figures, in which.

DETAILED DESCRIPTION OF THE EXEMPLARY EMBODIMENTS

Figure 1:
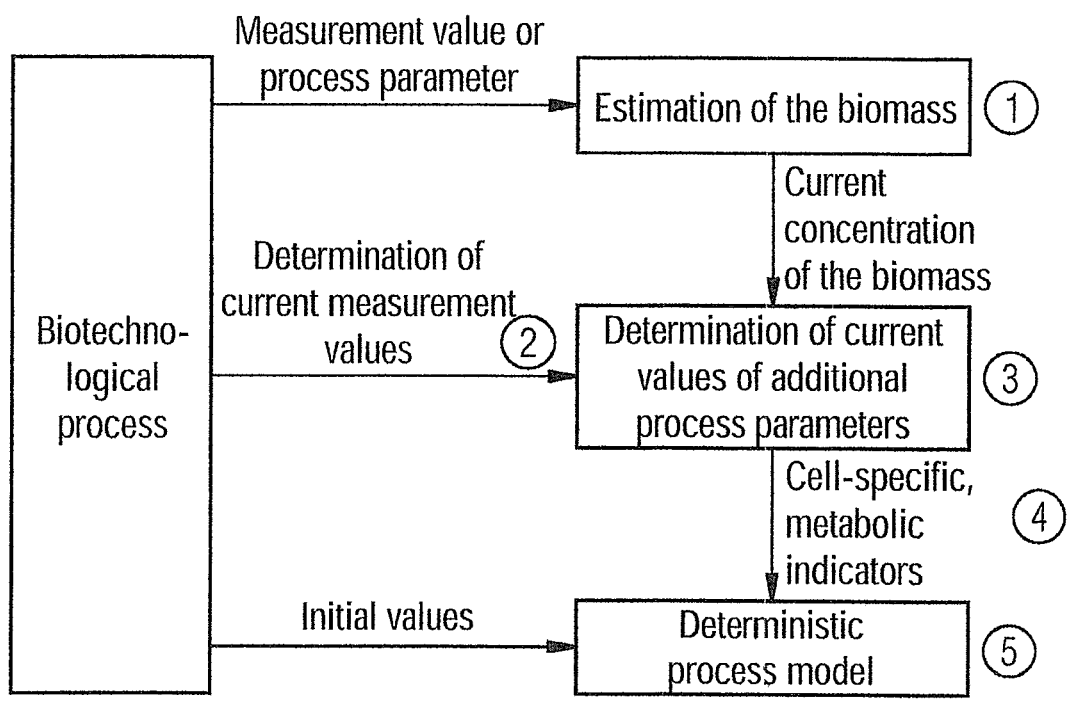
FIG. 1 shows a diagrammatic view of an exemplary sequence of the method in accordance with the invention for monitoring a biotechnological process.

FIG. 1 shows a diagrammatic view of an exemplary sequence of the method in accordance with the invention for monitoring a biotechnological process, such as a batch fermentation in which yeast is used as biomass. In a batch fermentation, for example, a reaction vessel such as a fermenter is filled with the starting materials (for example, nutrients) and biomass. In the exemplary biotechnological process or the exemplary batch fermentation, for example, 61 g of biomass (yeast) is used as initial biomass and 56 g of glucose as the nutrient starting concentration. The initial biomass and the nutrient starting concentration also represent initial values or input variables for a deterministic process model with which metabolic and catabolic processes can be described during the biotechnological process. The course of the biotechnological process or yeast batch fermentation can be estimated with the aid of the deterministic process model. Furthermore, comparative values for cell-specific metabolic key figures, such as glucose concentration, ethanol concentration, or biomass, can be determined from the deterministic process model at any time during the process.

During the exemplary biotechnological process, the yeast batch fermentation, after the fermenter has been filled a reaction, occurs between biomass and starting materials (for example, glucose), the concentration of which continuously falls, to products, the concentration of which continuously increases. In yeast batch fermentation, for example, in a first phase the nutrient or glucose is consumed by the biomass or yeast. Part of the glucose is oxidized with oxygen to form carbon dioxide and part of the glucose is fermented to ethanol. In a second phase, the yeast cells are adapted, for example, to ethanol consumption, where the metabolism of the yeast cells is greatly reduced in this phase. The ethanol is then consumed in a third phase of the yeast batch fermentation.

During the biotechnological process, important measurable process parameters, such as oxygen consumption, carbon dioxide emissions and the "respiratory quotient" (RQ) derived therefrom can be observed. The oxygen consumption and the carbon dioxide emissions are determined for example, via an "off-gas analysis". Due to the metabolic processes during the biotechnological process or during the yeast batch fermentation, the fermenter medium is acidified to different degrees in the different phases. This is counteracted by adding base to keep a pH in the fermenter constant.

Therefore, in yeast batch fermentation, a base consumption can also be used or observed as a measurable process parameter. In other biotechnological processes, it is also possible, for example, to use an acid consumption as a measurable process parameter. Throughout the entire course of the process of exemplary yeast batch fermentation, the yeast cells used as biomass grow. This also means the biomass changes in the course of the process, where in yeast batch fermentation the biomass increases, for example.

Therefore, during the process of exemplary yeast batch fermentation, a current concentration of the biomass in the fermenter is estimated in a first method step 1. The current concentration of the biomass can be estimated, for example, via a suitable sensor system, such as a system for measuring the cell density of living cells and/or microorganisms (for example, Incyte from the company Hamilton). Alternatively, or optionally in addition, the current concentration of the biomass in the fermenter can also be estimated from measurable process parameters via a "statistical model". For example, a "Partial Least Squares" (PLS) model is used for this purpose, with the aid of which the concentration of the biomass is estimated from current values of, for example, oxygen consumption, carbon dioxide emissions, respiratory quotient and base consumption.

In a second method step 2, current measurement values of measurable process parameters are determined. All those process parameters for which current measurement values can be determined easily and rapidly (i.e., almost in real time) during the process can be used as measurable process parameters. For yeast batch fermentation, for example, the oxygen consumption and/or carbon dioxide emissions can be measured very simply during the process. Measurement performed, for example, via the "off-gas analysis". Furthermore, a base consumption can be determined very easily at any time in the course of the process, for example, by measuring a weight of the base that has not yet been added to the fermenter.

Associated current values for additional process parameters are then determined from the current measurement values of the measurable process parameters in a third method step 3. In this connection, derived consumption and production variables as additional process parameters, in particular consumption of nutrients or glucose, production of a substance or ethanol and/or a growth of biomass. Furthermore, current values for material conversion rates and/or production rates can also be determined. The current values of the additional production parameters are determined in the third method step 3 with the aid of a "balancing process model".

For example, the chemical equations describing the respective biotechnological process, for example, the yeast-batch fermentation, are used by the balancing process model. The individual metabolic pathways for metabolism and anabolism (i.e., cell growth) of the respective process are described by these chemical equations. In yeast batch fermentation, for example, metabolic pathways are used for the balancing process model, which describe glucose oxidation and glucose fermentation in the first process phase and ethanol consumption in the second process phase and above all in the third process phase. Here, the current measurement values of the easily measurable process parameters "oxygen consumption" and "carbon dioxide emissions" are used as input values for the balancing process model and, taking into account a nitrogen balance for estimating the biogrowth, the current values of a glucose and ethanol concentration are determined from the balancing model as additional process parameters for yeast batch fermentation.

The current measurement values of the measurable process parameters as well as the corresponding current values of the additional process parameters, which were determined from the current measurement values of the measurable process parameters, are related to the corresponding current (i.e., time-correlated) concentration of the biomass. In a fourth method step 4, current cell-specific metabolic indicators are then derived therefrom. These current cell-specific metabolic indicators can include, for example, for yeast batch fermentation, cell-specific uptake rates of oxygen and glucose, cell-specific conversion or production rates, such as cell-specific rates of oxidized glucose and/or glucose fermented to ethanol, specific cell growth, or cell-specific carbon dioxide emissions.

Furthermore, the current values of the cell-specific metabolic indicators and/or a respective temporal change of the cell-specific metabolic indicators can be output on a display unit. An operator thereby obtains a comprehensive picture of the biological and biochemical processes during the process and can make decisions and provisions directly based on the biological information obtained or the current values of the cell-specific metabolic indicators.

Furthermore, the respective current cell-specific metabolic indicators can be compared with corresponding, time-correlated comparative values in a fifth method step 5. These comparative values are calculated, for example, with the aid of the deterministic process model with which, for example, metabolic and catabolic processes in the biotechnological process can be described during a process development. As initial values for the deterministic process model, in the yeast batch fermentation described by way of example—as already stated—the weighed initial biomass (yeast) and the nutrient starting concentration (glucose amount) were used. If differences or deviations between one or more current, cell-specific metabolic indicators and the respective comparative value(s) are determined in the comparison that are greater than anticipated static fluctuations, appropriate correction and/or verification measures can be initiated. For example, if due to process management no changes in cell-specific metabolic indicators (for example, conversion rates) are to be expected or if the deviations cannot be explained by changes in cell-specific metabolic indicators, then measurement errors in the sensors (for example, oxygen probe, or $CO_2$ probe) can be concluded from the observed deviations. Furthermore, the deviations can be used to intervene in the process, if appropriate, in a regulating manner.

As with the method in accordance with the invention, the current concentration of biomass, the current measurement values of the measurable process parameters and the current values of the additional process parameters and thus also the current, cell-specific metabolic indicators are periodically recurrently determined, even small errors can be rapidly detected in the fifth method step 5.

Alternatively, the cell-specific metabolic indicator values derived in the fourth method step 4 can also be used in a process prediction in the case of varying process management. For this purpose, currently determined values of the cell-specific metabolic indicators are virtually adopted as initial values by the deterministic process model in the fifth method step 5 to predict a further course of the process, such as a time of the end of the process or an expected product quantity. In this way, for example, effects of changing environmental conditions (for example, temperature, pH, or medium or oxygen supply) on the conversion rates can be estimated. Furthermore, in this way, the deterministic model for a new biotechnological process, for example, with a new yeast strain, or with another biomass, can be adapted and parameterized rapidly.

In the method in accordance with the invention, the current concentration of the biomass, the current measurement values of the measurable process parameters and the current values of the additional process parameters and thus also the current, cell-specific metabolic indicators are periodically recurrently determined with a temporal frequency. This means that at least the first four method steps 1 to 4 are periodically recurrently performed at a repetition frequency. These first four process steps 1 to 4 can be combined, for example, to form a measuring cycle that is repeated at the repetition frequency or at the time frequency. This temporal frequency or repetition frequency can be determined as a function of the biomass used. For example, in yeast batch fermentation, the refresh rate can be set at once per minute.

For an exemplary practical application of the method in accordance with the invention, the fermenter can be controlled, for example, using a process control system, such as the Simatic PCS7. During the method in accordance with the invention, the current values of the measurable process parameters and/or the off-gas analysis values, such as at the specified repetition frequency (for example, once per minute), are transmitted via an interface to a Process Analytical Technology (PAT) system, such as Simatic SIPAT. A Process Analytical Technology System is used to optimize, analyze and control manufacturing processes in the chemical and biotechnology industries.

The Process Analytical Technology System then triggers the first method step 1 at the repetition frequency, such as once a minute, in order to estimate the current concentration of the biomass either via suitable sensors or with the aid of the statistical model. The second and third method steps 2, 3 are then triggered by the Process Analytical Technology System to obtain current measurement values of the measurable process parameters and current values of the additional process parameters from the balancing process model. In the fourth method step 4, the current cell-specific metabolic indicators are then derived, which are then compared with the comparative values calculated by the deterministic process model in the fifth method step 5 for process management and error analysis. Alternatively, in the fifth method step 5, the further course of a process can be calculated as initial values with the deterministic process model and the current cell-specific metabolic indicators.

After passing through the method steps 1 to 4 or method steps 1 to 5, the measuring cycle is started again and passed through with new, current measurement values of measurable process parameters (for example, biomass, oxygen consumption, carbon dioxide emissions).

The method in accordance with the invention was described by way of example based on a yeast batch fermentation and/or a batch method. However, it can also be used for other biotechnological processes in which, for example, the "fed batch method" is used.

Figure 2:
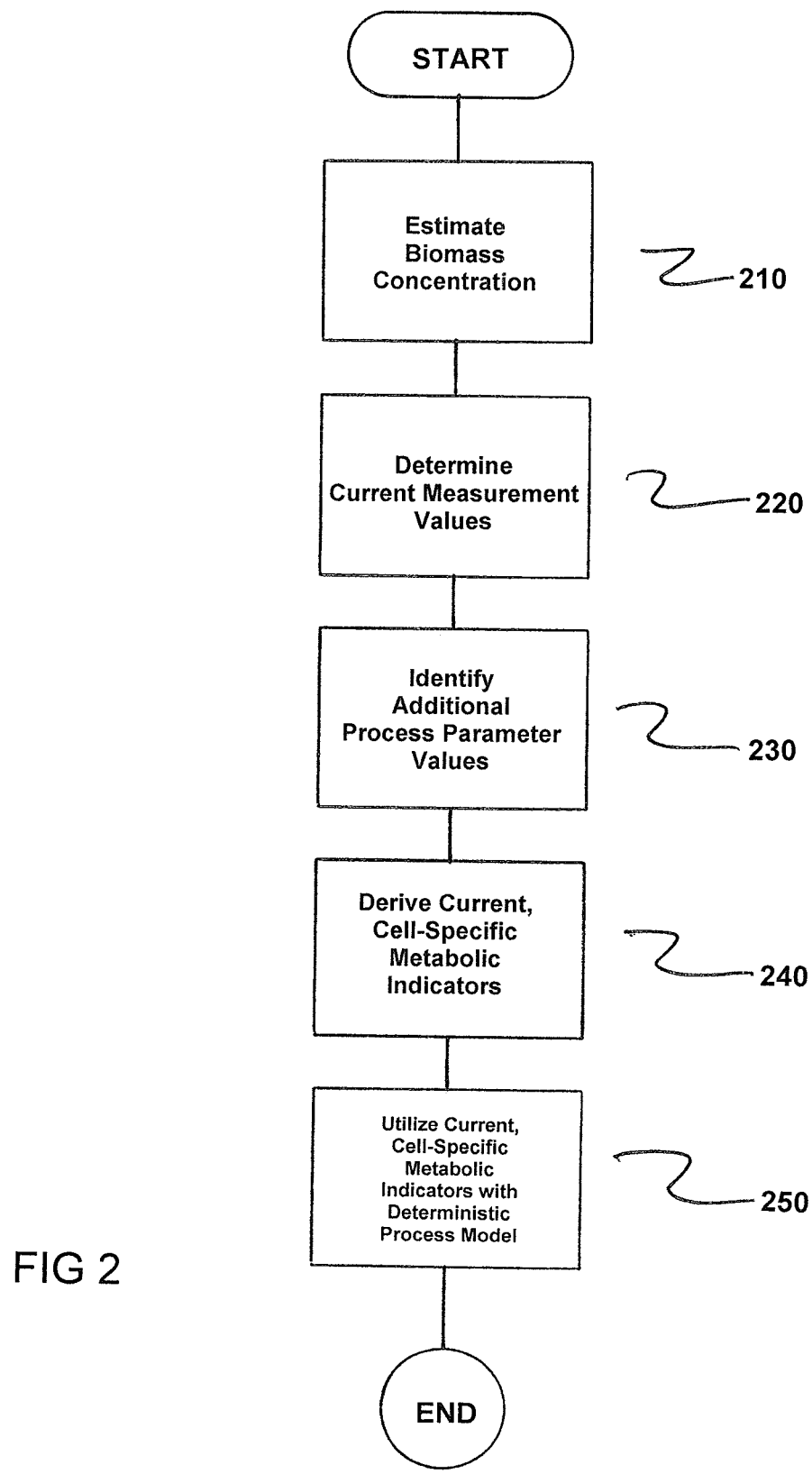
FIG. 2 is a flowchart of the method in accordance with the invention.

FIG. 2 is a flowchart of the method for monitoring a biotechnological process, where starting materials are converted into products via a biomass during the process and important process parameters are identified.

The method comprises recurrently estimating (1) a current concentration of the biomass used in the process during the biotechnological process, an indicated in step 210.

Next, current measurement values of measurable process parameters are recurrently determined (2), as indicated in step 220. Next, current values for additional process parameters from the current measurement values of the measurable process parameters are identified (3), as indicated in step 230.

Next, current, cell-specific metabolic indicators are derived (4), as indicated in step 240. In accordance with the invention, the current measurement values of the measurable process parameters and current determined values of the additional process parameters are based on a respective temporally correlating concentration of biomass from which the current, cell-specific metabolic indicators are derived.

Next, the current, cell-specific metabolic indicators, in conjunction with a deterministic process model, are now utilized (5), as indicated in step 250.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for monitoring a biotechnological process, starting materials being converted into products via a biomass during the biotechnological process and important process parameters being identified, the method comprising:
    estimating, recurrently, a current concentration of the biomass used in the process during the biotechnological process;
    determining, recurrently, current measurement values of measurable process parameters;
    identifying current values for additional process parameters from the current measurement values of the measurable process parameters;
    deriving current, cell-specific metabolic indicators, the current measurement values of the measurable process parameters and current determined values of the additional process parameters being based on a respective temporally correlating concentration of biomass from which the current, cell-specific metabolic indicators are derived; and
    utilizing the current, cell-specific metabolic indicators in conjunction with a deterministic process model.

2. The method as claimed in claim 1, wherein the current values of the additional process parameters are calculated via a balancing process model from the measured current values of the measurable process parameters.

3. The method as claimed in claim 2, wherein process parameters for which current measurement values are determinable substantially in real-time during the biotechnological process are utilized as measurable process parameters.

4. The method as claimed in claim 2, wherein consumption and production volumes derivable as additional process parameters are utilized during said identifying step.

5. The method as claimed in claim 1, wherein process parameters for which current measurement values are determinable substantially in real-time during the biotechnological process are utilized as measurable process parameters.

6. The method as claimed in claim 5, wherein consumption and production volumes derivable as additional process parameters are utilized during said identifying step.

7. The method as claimed in claim 1, wherein consumption and production volumes derivable as additional process parameters are utilized during said identifying step.

8. The method as claimed in claim 1, wherein a sensor system is utilized to estimate the respective current concentration of the biomass.

9. The method as claimed in claim 1, wherein a statistical model is utilized to estimate the respective current concentration of the biomass.

10. The method as claimed in claim 1, wherein the current, cell-specific metabolic indicators are compared with time-correlated, calculated comparative values for said cell-specific metabolic indicators;
wherein the deterministic process model is utilized to calculate the comparative values; and
wherein in an event of a difference between the current cell-specific metabolic indicators and the time-correlated calculated comparative values, at least one of correction and checking measures are initiated.

11. The method as claimed in claim 10, wherein measurement errors in the sensors utilized are concluded from the difference between the current cell-specific metabolic indicators and the time-correlated comparative values from the deterministic process model.

12. The method as claimed in claim 1, wherein the current, cell-specific metabolic indicators are utilized as initial values for the deterministic process model.

13. The method as claimed in claim 1, wherein a time frequency is established to estimate the respective current concentration of the biomass and to determine the current measured values of the measurable process parameters and the current values of the additional process parameters as a function of the biomass utilized.

14. The method as claimed in claim 1, wherein the current, cell-specific metabolic indicators are output on a display unit.

15. The method as claimed in claim 1, wherein the biomass comprises at least one of living cells and microorganisms.

* * * * *